US012115525B2

(12) United States Patent
Takada et al.

(10) Patent No.: US 12,115,525 B2
(45) Date of Patent: Oct. 15, 2024

(54) METHOD FOR PURIFYING ORGANIC SOLVENT AND APPARATUS FOR PURIFYING ORGANIC SOLVENT

(71) Applicant: ORGANO CORPORATION, Tokyo (JP)

(72) Inventors: Noriko Takada, Tokyo (JP); Haruo Yokota, Tokyo (JP); Yui Shioya, Tokyo (JP); Yasuhiro Yoshimura, Tokyo (JP)

(73) Assignee: ORGANO CORPORATION, Tokyo (JP)

( * ) Notice: Subject to any disclaimer, the term of this patent is extended or adjusted under 35 U.S.C. 154(b) by 502 days.

(21) Appl. No.: 17/606,213

(22) PCT Filed: Apr. 1, 2020

(86) PCT No.: PCT/JP2020/015101
§ 371 (c)(1),
(2) Date: Oct. 25, 2021

(87) PCT Pub. No.: WO2020/217911
PCT Pub. Date: Oct. 29, 2020

(65) Prior Publication Data
US 2022/0234037 A1    Jul. 28, 2022

(30) Foreign Application Priority Data

Apr. 26, 2019  (JP) ................. 2019-085989

(51) Int. Cl.
*B01J 47/028*     (2017.01)
*B01J 39/19*      (2017.01)
(Continued)

(52) U.S. Cl.
CPC ............. *B01J 47/028* (2013.01); *B01J 39/19* (2017.01); *B01J 41/14* (2013.01); *B01J 47/04* (2013.01)

(58) Field of Classification Search
CPC ... B01J 39/05; B01J 45/00; B01J 41/05; B01J 47/028; B01J 47/04
See application file for complete search history.

(56) References Cited

U.S. PATENT DOCUMENTS

| 4,182,676 A | * | 1/1980 | Casolo ..................... B01J 39/05 |
| | | | 210/686 |
| 5,951,874 A | * | 9/1999 | Jangbarwala ............ B01J 49/08 |
| | | | 210/678 |
| 2019/0009266 A1 | | 1/2019 | Ohba et al. |

FOREIGN PATENT DOCUMENTS

| JP | 6-220102 A | 8/1994 |
| JP | 7-208166   | 8/1995 |

(Continued)

OTHER PUBLICATIONS

Duolite C467 Data Sheet (Year: 2023).*

(Continued)

*Primary Examiner* — Bradley R Spies
(74) *Attorney, Agent, or Firm* — GREENBLUM & BERNSTEIN, P.L.C.

(57) ABSTRACT

A method for purifying an organic solvent has a first treatment of bringing an organic solvent to be treated into contact with an H-type cation exchanger, and a second treatment of bringing a treated liquid from the first treatment into contact with an anion exchanger and an H-type strongly acidic cation exchanger. According to the present application, the provided method and an apparatus for purifying an organic solvent remove metal impurities of both metal species of monovalent and polyvalent metals in the organic solvent.

11 Claims, 2 Drawing Sheets

(51) Int. Cl.
    *B01J 41/14*     (2006.01)
    *B01J 47/04*     (2006.01)

(56) References Cited

FOREIGN PATENT DOCUMENTS

| | | |
|---|---|---|
| JP | 10-25256 | 1/1998 |
| JP | 2003-535836 | 12/2003 |
| JP | 2005-232093 | 9/2005 |
| JP | 2013-23442 | 2/2013 |
| JP | 2019-509882 A | 4/2019 |
| KR | 10-2008-0037050 A | 4/2008 |
| KR | 10-2018-0059472 A | 6/2018 |

OTHER PUBLICATIONS

Fukumura et al—JP07208166A machine translation (Year: 1995).*
Kato—JP2005232093 A machine translation (Year: 2005).*
Official Communication issued in International Patent Application No. PCT/JP2020/015101 dated Jul. 7, 2020, along with English translation thereof.
Office Action issued Nov. 10, 2023 in Korean family member application No. 10-2021-7031031 with English language translation thereof.
Office Action drafted Jan. 11, 2024 in Japanese family member Patent Application No. 2021-515931 with English language translation.
Office Action dated Dec. 8, 2023 in Taiwanese family member Application No. 109112431 with English language translation.
Office Action dated Jun. 15, 2023 in Taiwanese Patent Application No. 109112431 and English translation thereof.

* cited by examiner

[FIG. 1]
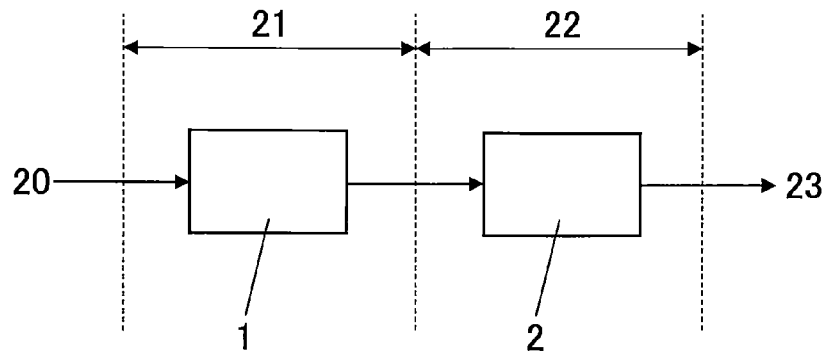
[FIG. 2]
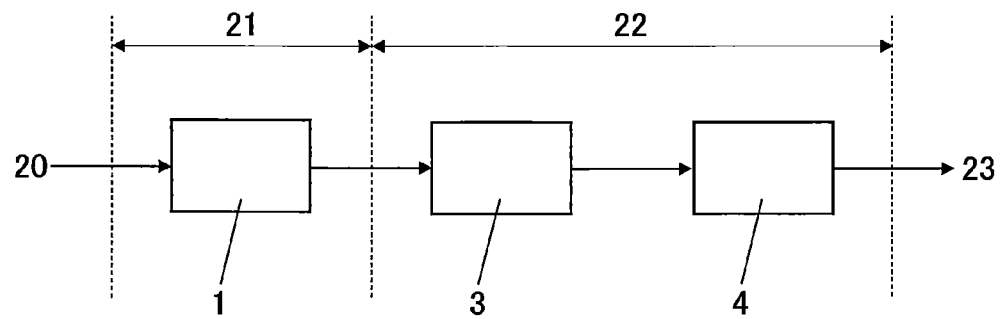
[FIG. 3]
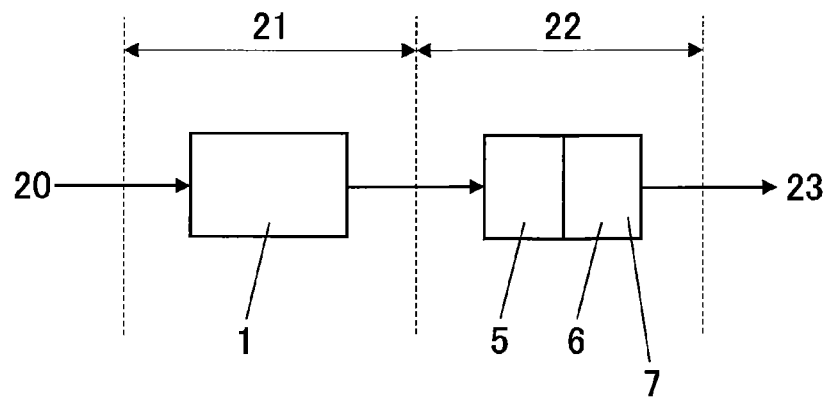

[FIG. 4]
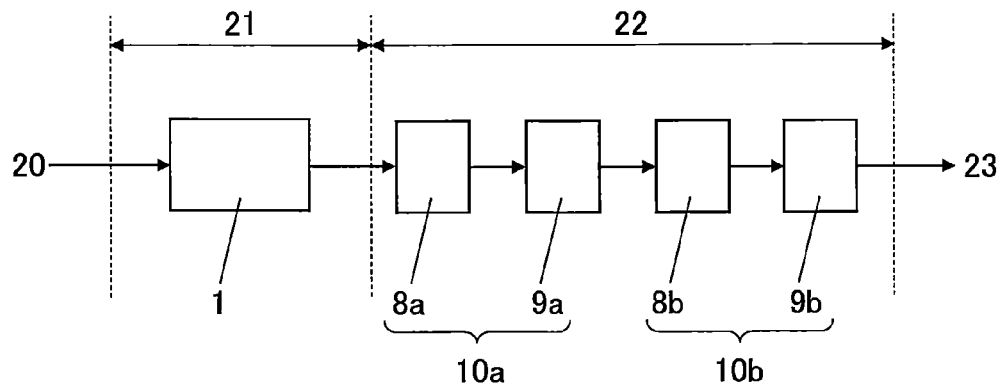
[FIG. 5]
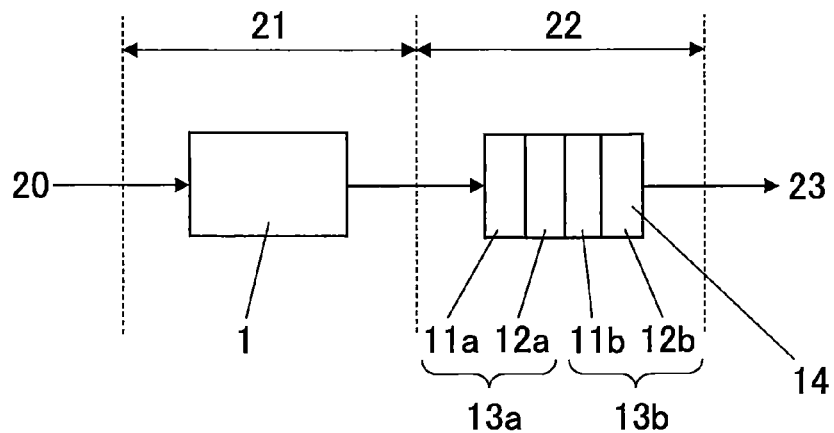
[FIG. 6]
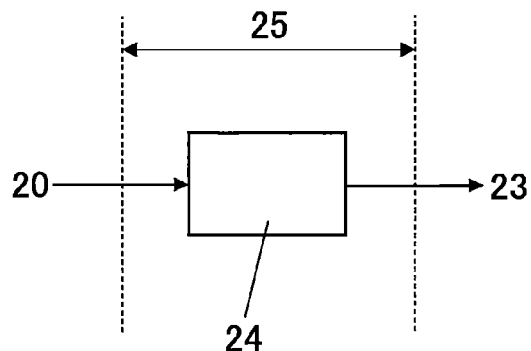

METHOD FOR PURIFYING ORGANIC SOLVENT AND APPARATUS FOR PURIFYING ORGANIC SOLVENT

TECHNICAL FIELD

The present invention relates to a method for purifying an organic solvent in order to obtain a high-purity organic solvent reduced in the metal impurity content, and an apparatus for purifying an organic solvent to carry out the method.

BACKGROUND ART

In semiconductor production processes, metal impurities contained in isopropyl alcohol (IPA) used for cleaning are highly likely to adversely affect wafers, and therefore the impurity content of IPA needs to be reduced to the ppt level.

Methods for removing metal impurities in organic solvents to purify the organic solvents include methods using ion exchangers, and it is known that by ion exchangers having strongly acidic cation-exchange groups, including ion-exchange resins and ion adsorption membranes, metal impurities in the organic solvents can be reduced to the ppt level.

For example, Patent Literature 1 discloses a method for producing a high-purity isopropanol having a metal content of lower than 1 ppb and a water content of lower than 100 ppm, the method including (a) a step of feeding, to a separation column, a feed material flow containing at least 99.9% by weight of isopropyl alcohol, 200 to 500 ppm of organic impurities and 100 ppm or lower of water, (b) a step of separating the feed material flow into a head flow collected from an upper part of the separation column and containing concentrated components having lower boiling points than isopropyl alcohol, and a bottom flow collected from a bottom of the separation column and containing concentrated components having higher boiling points than isopropyl alcohol, wherein isopropyl alcohol contained in the head flow and the bottom flow is not a high-purity isopropyl alcohol having a metal content of lower than 1 ppb and a water content of lower than 100 ppm, and (c) a step of obtaining, as a vapor side flow, the high-purity isopropyl alcohol at the following positions: (i) a position lower than a position where the feed material flow flows in the separation column and upper than the bottom flow, (ii) or a position upper than the position where the feed material flow flows in the separation column and lower than the head flow.

CITATION LIST

Patent Literature

[Patent Literature 1] National Publication of International Patent Application No. 2003-535836

SUMMARY OF INVENTION

Technical Problem

However, since the diffusion velocity of metal impurities is low and the reaction velocity of the ion-exchange reaction with ion-exchange resins is low in organic solvents, in the case of carrying out removal of ionic impurities in organic solvents, the liquid passing velocity with respect to ion-exchange resins is set to be lower than that for the case of removing the ionic impurities in aqueous solutions. For example, in the case of a process using a strongly acidic cation-exchange resin, it is difficult to obtain the same metal removal rate as in a case in water.

Then, the present inventors have found that it is difficult to diminish all of metals in a solvent such as IPA by using a strongly acidic cation exchanger, and in particular, metals poor in the removal rate, such as Cr and As, are present.

Thus, an object of the present invention is to provide a method and an apparatus for purifying an organic solvent, being excellent in the removability of metal impurities of both monovalent and polyvalent metal species in the organic solvent.

Solution to Problem

In view of such a background art, the present inventors have conducted exhaustive studies to find that (1) di- or higher-valent metals such as Cr are poor in the removal rate by a strongly acidic cation-exchange resin; further, some metals among these metals possibly have an anion form in an organic solvent, and then, in order to remove these metals, use of an H-type chelate exchanger is effective; when the H-type chelate exchanger is used, trace amounts of mineral acids such as hydrochloric acid present in the H-type chelate exchanger migrate into a treated liquid, which poses such a new problem that the mineral acids originated from the H-type chelate exchanger results in being contained in the treated liquid; and in order to solve the problem, it is effective that the liquid treated with the H-type chelate exchanger is treated with an anion exchanger and a strongly acidic ion exchanger, (2) after mono-, di- and more pentavalent metals in an organic solvent are removed by an H-type strongly acidic cation exchanger, by treating the treated liquid further with an anion exchanger and an H-type strongly acidic ion exchanger, metals such as Cr having an anion form are removed by the anion exchanger, and the another contact with the strongly acidic ion exchanger can effectively remove the mono-, di- and more pentavalent metals which have not completely been removed in the former stage, and the like, and these findings have led to the completion of the present invention.

That is, the present invention (1) provides a method for purifying an organic solvent, comprising:
  a first treatment step of bringing an organic solvent to be treated into contact with an H-type cation exchanger (1); and
  a second treatment step of bringing a treated liquid from the first treatment step into contact with an anion exchanger (2) and an H-type strongly acidic cation exchanger (3).

Then, the present invention (2) provides the method for purifying an organic solvent according to (1), wherein the second treatment step is carried out by passing the treated liquid from the first treatment step through a mixed bed of the anion exchanger (2) and the H-type strongly acidic cation exchanger (3).

Then, the present invention (3) provides the method for purifying an organic solvent according to (1), wherein the second treatment step is carried out by first bringing the treated liquid from the first treatment step into contact with the anion exchanger (2), and then bringing the treated liquid into contact with the H-type strongly acidic cation exchanger (3).

Then, the present invention (4) provides the method for purifying an organic solvent according to any one of (1) to (3), wherein the H-type cation exchanger (1) is an H-type chelate exchanger.

Then, the present invention (5) provides the method for purifying an organic solvent according to any one of (1) to (3), wherein the H-type cation exchanger (1) is an H-type strongly acidic cation exchanger.

Then, the present invention (6) provides a method for purifying an organic solvent, comprising a treatment step of bringing an organic solvent to be treated into contact with a mixed bed of an H-type chelate exchanger, an anion exchanger (2) and an H-type strongly acidic cation exchanger (3).

Then, the present invention (7) provides the method for purifying an organic solvent according to (4) or (6), wherein a functional group of the H-type chelate exchanger is an iminodiacetic acid group, an aminomethylphosphoric acid group or an iminopropionic acid group.

Then, the present invention (8) provides the method for purifying an organic solvent according to any one of (4), (6) and (7), wherein the proportion of a volume of the anion exchanger to a volume of the H-type chelate exchanger is 0.1 to 99.0% by volume.

Then, the present invention (9) provides the method for purifying an organic solvent according to any one of (4), and (6) to (8), wherein the proportion of a volume of the cation exchanger (2) to a volume of the H-type chelate exchanger is 0.1 to 99.0% by volume.

Then, the present invention (10) provides the method for purifying an organic solvent according to any one of (1) to (9), wherein the organic solvent is a polar organic solvent.

Then, the present invention (11) provides an apparatus for purifying an organic solvent, comprising a single bed of an H-type cation exchanger (1) through which an organic solvent to be treated is passed, and a mixed bed of an anion exchanger (2) and an H-type strongly acidic cation exchanger (3) through which a treated liquid from the single bed of the H-type cation exchanger (1) is passed.

Then, the present invention (12) provides an apparatus for purifying an organic solvent, comprising a single bed of an H-type cation exchanger (1) through which an organic solvent to be treated is passed, a single bed of an anion exchanger (2) through which a treated liquid from the single bed of the H-type cation exchanger (1) is passed, and a single bed of an H-type strongly acidic cation exchanger (3) through which a treated liquid from the single bed of the anion exchanger (2) is passed.

Then, the present invention (13) provides an apparatus for purifying an organic solvent comprising a mixed bed of an H-type chelate exchanger, an anion exchanger (2) and an H-type strongly acidic cation exchanger (3) through which an organic solvent to be treated is passed.

Advantageous Effect of Invention

According to the present invention, there can be provided a purification method and a purification apparatus excellent in the removability of metal impurities of both metal species of monovalent metals and polyvalent metals in an organic solvent.

BRIEF DESCRIPTION OF DRAWINGS

FIG. 1 is a schematic flow diagram showing a first form of a second treatment step of a method for purifying an organic solvent according to a first embodiment or a second embodiment of the present invention.

FIG. 2 is a schematic flow diagram showing a second form of the second treatment step of the method for purifying an organic solvent according to the first embodiment or the second embodiment of the present invention.

FIG. 3 is a schematic flow diagram showing a third form of the second treatment step of the method for purifying an organic solvent according to the first embodiment or the second embodiment of the present invention.

FIG. 4 is a schematic flow diagram showing a fourth form of the second treatment step of the method for purifying an organic solvent according to the first embodiment or the second embodiment of the present invention.

FIG. 5 is a schematic flow diagram showing a fifth form of the second treatment step of the method for purifying an organic solvent according to the first embodiment or the second embodiment of the present invention.

FIG. 6 is a schematic flow diagram showing a method for purifying an organic solvent according to a third embodiment of the present invention.

DESCRIPTION OF EMBODIMENTS

A method for purifying an organic solvent according to a first embodiment of the present invention is a method for purifying an organic solvent comprising:
  a first treatment step of bringing an organic solvent to be treated into contact with an H-type chelate exchanger (1a); and
  a second treatment step of bringing a treated liquid from the first treatment step into contact with an anion exchanger (2) and an H-type strongly acidic cation exchanger (3).

The first treatment step involved in the method for purifying an organic solvent according to the first embodiment of the present invention is a step of bringing the organic solvent to be treated into contact with the H-type chelate exchanger (1a).

The organic solvent to be treated involved in the method for purifying an organic solvent according to the first embodiment of the present invention is not especially limited, and examples thereof include alcohols such as isopropyl alcohol, methanol and ethanol, ketones such as cyclohexanone, methyl isobutyl ketone, acetone and methyl ethyl ketone, alkene organic solvents such as 2,4-diphenyl-4-methyl-1-pentene and 2-phenyl-1-propene, and N-methylpyrrolidone, and mixed organic solvents thereof. The organic solvent to be treated may be either of a polar organic solvent and a non-polar organic solvent, and a polar organic solvent is preferable. The polar organic solvent may be a protonic polar organic solvent, or may also be an aprotic organic solvent.

The organic solvent to be treated contains, as metal impurities, both of monovalent metals such as Na, K and Li, and di- and higher-valent metals, such as Cr, As, Ca, Cu, Fe, Mg, Mn, Ni, Pb and Zn, which are easily removed with chelate resins.

The content of each metal impurity in the organic solvent to be treated is not especially limited, and is usually about 100 ppb by mass to 20 ppt by mass.

The H-type cation exchanger (1) involved in the method for purifying an organic solvent according to the first embodiment of the present invention is the H-type chelate exchanger (1a).

The H-type chelate exchanger (1a) is a substance made by bringing a chelate exchanger of a metal ion type such as Na, Ca or Mg type into contact with a mineral acid for the chelate exchanger to be acid treated and converted to an H-type one. That is, the H-type chelate exchanger (1a) is a mineral acid-contacted and treated substance of a metal ion-type chelate exchanger.

A functional group the H-type chelate exchanger (1a) is not especially limited as long as being capable of coordinating to a metal ion and forming a chelate, and examples thereof include functional groups having an amino group, such as an iminodiacetic acid group, an aminomethylphosphoric acid group and an iminopropionic acid group, and a thiol group. Among these, the functional group of the chelate exchanger is, in that the removability of a large number of polyvalent metal ions becomes high, preferably functional groups having an amino group, and especially preferably an iminodiacetic acid group, an aminomethylphosphoric acid group and an iminopropionic acid group.

The H-type chelate exchanger (1a) includes granular H-type chelate exchange resins. The substrate of the H-type chelate exchange resin includes styrene-divinylbenzene copolymers. The H-type chelate exchange resin may be of any structure of a gel structure, a macroporous structure and a porous structure. The exchange capacity of the H-type chelate exchange resin is preferably 0.5 to 2.5 eq/L-R and especially preferably 1.0 to 2.5 eq/L-R. The mean particle diameter (harmonic mean diameter) of the H-type chelate exchange resin is not especially limited, and is preferably 300 to 1,000 μm and especially preferably 500 to 800 μm. Here, the mean particle diameter of the H-type chelate exchange resin is a value measured by a laser diffraction type particle size distribution analyzer.

Then, the H-type chelate exchanger (1a) includes H-type organic porous chelate exchangers. The H-type organic porous chelate exchanger is an organic porous material in which a functional group having a chelating ability, for example, an above-cited functional group having a chelating ability, is introduced. The exchange capacity of the H-type organic porous chelate exchanger is preferably 0.3 to 2 mg eq/mL (in a water-wet state) and especially preferably 1 to 2 mg eq/mL (in a water-wet state).

The H-type chelate exchanger (1a) is obtained by bringing a chelate exchanger of a metal ion type such as Na, Ca or Mg type into contact with a mineral acid for the chelate exchanger to be acid treated. The mineral acid for the metal ion-type chelate exchanger to be brought into contact with includes hydrochloric acid, sulfuric acid and nitric acid. Among these, the mineral acid is, in the point of safety, preferably hydrochloric acid and sulfuric acid. Then in the case of conversion from a Ca type, hydrochloric acid is preferable because use of sulfuric acid has a fear of deposition of calcium sulfate. The concentration of the mineral acid is preferably 0.1 to 6N and especially preferably 1 to 4N.

A method of bringing the metal ion-type chelate exchanger into contact with the mineral acid is not especially limited, and there are suitably selected the contact mode, the contact temperature, the contact time and the like.

After the metal ion-type chelate exchanger is brought into contact with the mineral acid, the H-type chelate exchanger converted to an H-type is washed with water to carry out removing surplus mineral acid, but since the functional group in the chelate exchanger is bonded with mineral acid through hydrogen bond and the like, the surplus mineral acid cannot completely be removed by washing with water. Hence, mineral acid used for the acid treatment remains in the H-type chelate exchanger.

Examples of the metal ion-type chelate exchange resin include CR-10 and CR-11, manufactured by Mitsubishi Chemical Corp., Duolite C-467, manufactured by Sumitomo Chemtex Co., Ltd., MC-700, manufactured by Sumitomo Chemical Co., Ltd., Lewatit TP207, Lewatit TP208 and Lewatit TP260, manufactured by Lanxess AG, 5930 and 5950, manufactured by Purolite Co., and DS-21 and DS-22, manufactured by Organo Corp.

In the first treatment step, by bringing the organic solvent to be treated into contact with the H-type chelate exchanger (1a), the organic solvent to be treated is treated with the H-type chelate exchanger (1a) to remove mainly divalent or higher-valent metals and a part of monovalent metals in the organic solvent to be treated.

In the first treatment step, the liquid passing velocity (SV) when the organic solvent to be treated is passed through the H-type chelate exchanger (1a) is not especially limited, and is suitably selected, but is preferably 0.1 to 100 $h^{-1}$, especially preferably 2 to 30 $h^{-1}$ and further preferably 4 to 25 $h^{-1}$.

In the first treatment step, the temperature when the organic solvent to be treated is passed through the H-type chelate exchanger (1a) is not especially limited, and is suitably selected, but is usually 0 to 50° C. Depending on the kind of the organic solvent to be treated, in the first treatment step, the organic solvent to be treated may also be passed through the H-type chelate exchanger (1a) at 0 to 80° C.

The second treatment step involved in the method for purifying an organic solvent according to the first embodiment of the present invention is a step of bringing the treated liquid from the first treatment step into contact with the anion exchanger (2) and the H-type strongly acidic cation exchanger (3).

The anion exchanger (2) involved in the method for purifying an organic solvent of the first embodiment of the present invention includes a strongly basic anion exchanger (2a) having a strongly basic anion-exchange group as an anion-exchange group, and a weakly basic anion exchanger (2b) having a weakly basic anion-exchange group as an anion-exchange group.

The strongly basic anion-exchange group involved in the strongly basic anion exchanger (2a) includes OH-type quaternary ammonium groups. Then the weakly basic anion-exchange group involved in the weakly basic anion exchanger (2b) includes tertiary amino groups, secondary amino groups, primary amino groups and polyamine groups.

The anion exchanger (2) involved in the method for purifying an organic solvent according to the first embodiment of the present invention includes granular anion-exchange resins. The substrate of the anion-exchange resin is a styrene-divinylbenzene copolymer. The anion-exchange resin may be of any of a gel structure, a macroporous structure and a porous structure. The ion-exchange capacity of the anion-exchange resin in a wet state is preferably 0.5 to 2 (eq/L-R) and especially preferably 0.9 to 2 (eq/L-R). The harmonic mean diameter of the anion-exchange resin is preferably 400 to 900 μm and especially preferably 500 to 800 μm. Examples of the anion-exchange resin include Amberlite IRA900, 402, 96SB and 98, and Amberjet 4400, 4002 and 4010, manufactured by Dow Chemical Co., Diaion UBA120, PA306S, PA308, PA312, PA316, PA318L, WA21J and WA30, manufactured by Mitsubishi Chemical Corp., DS-2, DS-5 and DS-6, manufactured by Organo Corp., A400, A600, SGA550, A500, A501P, A502PS, A503, A100, A103S, A110, A111S and A133S, manufactured by Purolite Co., and Lewatit MonoPlus M500, M800, MP62WS and MP64, manufactured by Lanxess AG.

Then, the anion exchanger (2) includes organic porous anion exchangers. The organic porous anion exchanger is an organic porous material in which an anion-exchange group, for example, an above-cited strongly basic anion-exchange group or weakly basic anion-exchange group, is introduced. The exchange capacity of the organic porous anion exchanger is preferably 1 to 6 mg eq/mL (in a dry state) and especially preferably 2 to 5 mg eq/mL (in a dry state).

The H-type strongly acidic cation exchanger (3) involved in the method for purifying an organic solvent according to the first embodiment of the present invention is one having a strongly acidic cation-exchange group converted to an H type, such as a sulfonic acid group.

The H-type strongly acidic cation exchanger (3) includes granular strongly acidic cation-exchange resins. The substrate of the H-type strongly acidic cation-exchange resin is a styrene-divinylbenzene copolymer. The H-type strongly acidic cation-exchange resin may be of any of a gel structure, a macroporous structure and a porous structure. The ion-exchange capacity of the H-type strongly acidic cation-exchange resin in a wet state is preferably 1.5 to 3.0 (eq/L-R) and especially preferably 1.7 to 2.7 (eq/L-R). The harmonic mean diameter of the H-type strongly acidic cation-exchange resin is preferably 400 to 900 μm and especially preferably 500 to 800 μm. Examples of the H-type strongly acidic cation-exchange resin include Amberlite IR120B, IR124 and 200CT252 and Amberjet 1020, 1024, 1060 and 1220, manufactured by Dow Chemical Co., Diaion SK104, SK1B, SK110, SK112, PK208, PK212L, PK216, PK218, PK220, PK228, UBK08, UBK10 and UBK12, manufactured by Mitsubishi Chemical Corp., DS-1 and DS-4, manufactured by Organo Corp., C100, C100E, C120E, C100×10, C100×12 MB, C150, C160 and SGC650, manufactured by Purolite Co., and Lewatit MonoPlus S108H, SP112 and S1668, manufactured by Lanxess AG.

Then, the H-type strongly acidic cation exchanger (3) includes H-type organic porous strongly acidic cation exchangers. The H-type organic porous strongly acidic cation exchanger is an organic porous material in which a strongly acidic cation-exchange group, for example, an above-cited strongly acidic cation-exchange group, is introduced. The exchange capacity of the H-type organic porous strongly acidic cation exchanger is preferably 1 to 3 mg eq/mL (in a dry state) and especially preferably 1.5 to 3 mg eq/mL (in a dry state).

In the second treatment step, by bringing the treated liquid from the first treatment step into contact with the anion exchanger (2) and the H-type strongly acidic cation exchanger (3), the organic solvent to be treated is treated with the anion exchanger (2) and the H-type strongly acidic cation exchanger (3) to thereby remove the remainder of the monovalent metals which has not completely be removed by the H-type chelate exchanger (1a) in the first treatment step and the mineral acid released from the H-type chelate exchanger (1a). Then, the regeneration of the anion exchanger uses NaOH as a regenerant, but when washing is sufficiently carried out after the regeneration, almost no remaining of NaOH in the anion exchanger occurs. In the second treatment step, even if washing after regeneration of the anion exchanger (2) is poor and such a situation occurs that the residue of NaOH used as a regenerant is eluted, the H-type strongly acidic cation exchanger (3) in the second treatment step can remove Na.

As the anion exchanger (2) and the H-type strongly acidic cation exchanger (3) to be brought into contact with the liquid to be treated in the second treatment step, there may be used a mixture of an above-cited cation exchanger and anion exchanger in any proportions, or an ion exchanger commercially available as a mixed product of the anion exchanger (2) and the H-type strongly acidic cation exchanger (3). Examples of the mixed product of the anion exchanger (2) and the H-type strongly acidic cation exchanger (3) include DS-3, DS-7, MSPS2-1·DRY, EG-4A-HG, EG-5A-HG, ESP-1 and ESP-2, manufactured by Organo Corp., AmberTec UP6040, manufactured by DuPont de Nemours, Inc., and MB378, MB378LT, MB400, MB424, MB46, MB47/4914 and MB478, manufactured by Purolite Co.

In the second treatment step, the liquid passing velocity (SV) when the treated liquid from the first treatment step is passed through the anion exchanger (2) and the H-type strongly acidic cation exchanger (3) is not especially limited and is suitably selected, but is preferably 0.1 to 100 h$^{-1}$ and especially preferably 2 to 50 h$^{-1}$.

In the second treatment step, the temperature when the treated liquid from the first treatment step is passed through the anion exchanger (2) and the H-type strongly acidic cation exchanger (3) is not especially limited and is suitably selected, but is usually 0 to 50° C. Then, depending on the kind of the organic solvent to be treated, in the second treatment step, the treated liquid from the first treatment step may also be passed through the anion exchanger (2) and the H-type strongly acidic cation exchanger (3) at 0 to 80° C. In the case where in the second treatment step, the treated liquid from the first treatment step is passed through the anion exchanger (2) and the H-type strongly acidic cation exchanger (3) at 60 to 80° C., since the strongly basic anion exchanger (2a), when being used as the anion exchanger (2), is easily decomposed, the weakly basic anion exchanger (2b) is used as the anion exchanger (2).

A method for purifying an organic solvent according to a second embodiment of the present invention is a method for purifying an organic solvent comprising:
   a first treatment step of bringing an organic solvent to be treated into contact with an H-type strongly acidic cation exchanger (1b); and
   a second treatment step of bringing a treated liquid from the first treatment step into contact with an anion exchanger (2) and an H-type strongly acidic cation exchanger (3).

The first treatment step involved in the method for purifying an organic solvent according to the second embodiment of the present invention is a step of bringing the organic solvent to be treated into contact with the H-type strongly acidic cation exchanger (1b).

The organic solvent to be treated involved in the method for purifying an organic solvent according to the second embodiment of the present invention is the same as the organic solvent to be treated involved in the method for purifying an organic solvent according to the first embodiment of the present invention.

The H-type cation exchanger (1) involved in the method for purifying an organic solvent according to the second embodiment of the present invention is the H-type strongly acidic cation exchanger (1b). The H-type strongly acidic cation exchanger (1b) involved in the method for purifying an organic solvent according to the second embodiment of the present invention is the same as the H-type strongly acidic cation exchanger (3) involved in the method for purifying an organic solvent according to the first embodiment of the present invention.

In the first treatment step, by bringing the organic solvent to be treated into contact with the H-type strongly acidic cation exchanger (1b), the organic solvent to be treated is treated with the H-type strongly acidic cation exchanger (1b) to remove a part of di- or higher-valent metals and a part of monovalent metals in the organic solvent to be treated.

In the first treatment step, the liquid passing velocity (SV) when the organic solvent to be treated is passed through the H-type strongly acidic cation exchanger (1b) is not especially limited, and is suitably selected, but is preferably 0.1 to 100 h$^{-1}$ and especially preferably 2 to 30 h$^{-1}$.

In the first treatment step, the temperature when the organic solvent to be treated is passed through the H-type strongly acidic cation exchanger (1b) is not especially limited, and is suitably selected, but is usually 0 to 50° C. Depending on the kind of the organic solvent to be treated, in the first treatment step, the organic solvent to be treated may also be passed through the H-type strongly acidic cation exchanger (1b) at 0 to 80° C.

The second treatment step involved in the method for purifying an organic solvent according to the second embodiment of the present invention is a step of bringing the treated liquid from the first treatment step into contact with the anion exchanger (2) and the H-type strongly acidic cation exchanger (3).

The anion exchanger (2) involved in the method for purifying an organic solvent of the second embodiment of the present invention is the same as the anion exchanger (2) involved in the method for purifying an organic solvent of the first embodiment of the present invention. Further, the H-type strongly acidic cation exchanger (3) involved in the method for purifying an organic solvent of the second embodiment of the present invention is the same as the H-type strongly acidic cation exchanger (3) involved in the method for purifying an organic solvent of the first embodiment of the present invention.

In the method for purifying an organic solvent according to the second embodiment of the present invention, the H-type strongly acidic cation exchanger (1b) to be used in the first treatment step and the H-type strongly acidic cation exchanger (3) to be used in the second treatment step may be the same H-type strongly acidic cation exchanger or may be different H-type strongly acidic cation exchangers.

In the second treatment step, by bringing the treated liquid from the first treatment step into contact with the anion exchanger (2) and the H-type strongly acidic cation exchanger (3), the organic solvent to be treated is treated with the anion exchanger (2) and the H-type strongly acidic cation exchanger (3) to thereby remove the remainder of the di- and higher-valent metals and the remainder of the monovalent metals which have not completely be removed by the H-type strongly acidic cation exchanger (1b) in the first treatment step. Further, in the second treatment step, the anion exchanger removes metals possibly having metal ions in anionic forms, such as Cr and As, and acids such as mineral acids and organic acids.

Then, in the method for purifying an organic solvent according to the second embodiment of the present invention, by carrying out contacting in two or more stages in which the organic solvent to be treated, after being once brought into contact with the H-type strongly acidic cation exchanger, is again brought into contact with the H-type strongly acidic cation exchanger, the removal rate of di- or higher-valent metals is raised compared with the case where the organic solvent to be treated is brought into contact with the same amount of the H-type strongly acidic cation exchanger.

In the second treatment step, the liquid passing velocity (SV) when the treated liquid from the first treatment step is passed through the anion exchanger (2) and the H-type strongly acidic cation exchanger (3) is not especially limited, and is suitably selected, but is preferably 0.1 to 100 h$^{-1}$ and especially preferably 2 to 30 h$^{-1}$.

In the second treatment step, the temperature when the treated liquid from the first treatment step is passed through the anion exchanger (2) and the H-type strongly acidic cation exchanger (3) is not especially limited, and is suitably selected, but is usually 0 to 50° C. Then, depending on the kind of the organic solvent to be treated, in the second treatment step, the treated liquid from the first treatment step may also be passed through the anion exchanger (2) and the H-type strongly acidic cation exchanger (3) at 0 to 80° C. In the case where in the second treatment step, the treated liquid from the first treatment step is passed through the anion exchanger (2) and the H-type strongly acidic cation exchanger (3) at 0 to 80° C., since the strongly basic anion exchanger (2a), when being used as the anion exchanger (2), is easily decomposed, the weakly basic anion exchanger (2b) is used as the anion exchanger (2).

The following are included as forms of the second treatment step involved in the method for purifying an organic solvent according to the first embodiment of the present invention, and forms of the second treatment step involved in the method for purifying an organic solvent according to the second embodiment of the present invention.

In a first form of the second treatment step, the second treatment step is carried out by passing the treated liquid from the first treatment step through a mixed bed of the anion exchanger (2) and the H-type strongly acidic cation exchanger (3). The mixed bed of the anion exchanger (2) and the H-type strongly acidic cation exchanger (3) is composed of a mixture of the anion exchanger (2) and the H-type strongly acidic cation exchanger (3). In the case where the anion exchanger (2) is the organic porous anion exchanger, there is used the organic porous anion exchanger having a shape cut out into an optional size, for example, a cube of about 3 mm to about 10 mm in one side. Then, in the case where the H-type strongly acidic cation exchanger (3) is the organic porous strongly acidic cation exchanger, there is used the organic porous strongly acidic cation exchanger having a shape cut out into an optional size, for example, a cube of about 3 mm to about 10 mm in one side.

Form examples as the first form of the second treatment step of the method for purifying an organic solvent according to the first embodiment of the present invention and the method for purifying an organic solvent according to the second embodiment of the present invention include a method in which, as shown in FIG. 1, an organic solvent to be treated 20 is first passed through an H-type cation exchanger-packed column 1 which is packed with an H-type cation exchanger (H-type chelate exchanger (1a) or H-type strongly acidic cation exchanger (1b)), and then a treated liquid which has been treated through the H-type cation exchanger column 1 is passed through a mixed bed-packed column 2 which is packed with a mixture of an anion-exchange resin (2) and a strongly acidic cation-exchange resin (3) to thereby obtain a purified organic solvent 23. In the form example shown in FIG. 1, the range indicated by Reference Sign 21 is the first treatment step, and the range indicated by Reference Sign 22 is the second treatment step.

In a second form of the second treatment step, the second treatment step is carried out by passing the treated liquid from the first treatment step through a single bed of the anion exchanger (2) as a prestage, and then passing the treated liquid through a single bed of the H-type strongly acidic cation exchanger (3) as a poststage.

Form examples as the second form of the second treatment step of the method for purifying an organic solvent according to the first embodiment of the present invention and the method for purifying an organic solvent according to the second embodiment of the present invention include a method in which, as shown in FIG. 2, an organic solvent to be treated 20 is first passed through an H-type cation exchanger-packed column 1 which is packed with an H-type cation exchanger (H-type chelate exchanger (1a) or H-type strongly acidic cation exchanger (1b)), and then a treated liquid which has been treated through the H-type cation exchanger column 1 is passed through an anion exchanger-packed column 3 which is packed with an anion exchanger (2) and then, a treated liquid which has been treated through the anion exchanger-packed column 3 is passed through a strongly acidic cation exchanger-packed column 4 which is packed with a strongly acidic cation exchanger (3) to thereby obtain a purified organic solvent 23. In the form example shown in FIG. 2, the range indicated by Reference Sign 21 is the first treatment step, and the range indicated by Reference Sign 22 is the second treatment step.

In a third form of the second treatment step, the second treatment step is carried out by passing the treated liquid from the first treatment step through a multiple bed composed of a layer of the anion exchanger (2) as a prestage, and a layer of the H-type strongly acidic cation exchanger (3) as a poststage. In the case where the anion exchanger (2) is the organic porous anion exchanger, the organic porous anion exchanger of a desired thickness cut out after the inner diameter of a packing vessel or column is packed in the packing vessel or column. Then, in the case where the H-type strongly acidic cation exchanger (3) is the H-type organic porous cation exchanger, the H-type organic porous cation exchange of a desired thickness cut out after the inner diameter of the packing vessel or column is packed in the packing vessel or column.

Form examples as the third form of the second treatment step of the method for purifying an organic solvent according to the first embodiment of the present invention and the method for purifying an organic solvent according to the second embodiment of the present invention include a method in which, as shown in FIG. 3, an organic solvent to be treated 20 is first passed through an H-type cation exchanger-packed column 1 which is packed with an H-type cation exchanger (H-type chelate exchanger (1a) or H-type strongly acidic cation exchanger (1b)), and then a treated liquid which has been treated through the H-type cation exchanger-packed column 1 is passed through a multiple bed-packed column 7 which is packed with a multiple bed 7 composed of a layer 5 of the anion exchanger (2) as a prestage and a layer 6 of the H-type strongly acidic cation exchanger (3) as a poststage to thereby obtain a purified organic solvent 23. In the form example shown in FIG. 3, the range indicated by Reference Sign 21 is the first treatment step, and the range indicated by Reference Sign 22 is the second treatment step.

In a fourth form of the second treatment step, the second treatment step is carried out by passing the treated liquid from the first treatment step through a multiple bed in which there are repeated two or more sets of a repeating unit of a single bed of the anion exchanger (2) as a prestage and a single bed of the H-type strongly acidic cation exchanger (3) as a poststage.

Form examples as the fourth form of the second treatment step of the method for purifying an organic solvent according to the first embodiment of the present invention and the method for purifying an organic solvent according to the second embodiment of the present invention include a method in which, as shown in FIG. 4, an organic solvent to be treated 20 is first passed through an H-type cation exchanger-packed column 1 which is packed with an H-type cation exchanger (H-type chelate exchanger (1a) or H-type strongly acidic cation exchanger (1b)), and then a treated liquid which has been treated through the H-type cation exchanger-packed column 1 is passed through a "first repeating unit 10a composed of a packed column 8a of the anion exchanger (2) as a prestage and a packed column 9a of the H-type strongly acidic cation exchanger (3) as a poststage" and a "second repeating unit 10b composed of a packed column 8b of the anion exchanger (2) as a prestage and a packed column 9b of the H-type strongly acidic cation exchanger (3) as a poststage" in order, to thereby obtain a purified organic solvent 23. In the form example shown in FIG. 4, the range indicated by Reference Sign 21 is the first treatment step, and the range indicated by Reference Sign 22 is the second treatment step. Here, in the form example shown in FIG. 4, there has been shown an example in which there is twice repeated the repeating unit composed of the packed column of the anion exchanger (2) as a prestage and the packed column of the H-type strongly acidic cation exchanger (3) as a poststage, but there may be three or more times repeated the repeating unit composed of the packed column of the anion exchanger (2) as a prestage and the packed column of the H-type strongly acidic cation exchanger (3) as a poststage.

In a fifth form of the second treatment step, the second treatment step is carried out by passing the treated liquid from the first treatment step through a multiple bed in which there are laminated two or more sets of a repeating unit of a layer of the anion exchanger (2) as a prestage and a layer of the H-type strongly acidic cation exchanger (3) as a poststage.

Form examples as the fifth form of the second treatment step of the method for purifying an organic solvent according to the first embodiment of the present invention and the method for purifying an organic solvent according to the second embodiment of the present invention include a method in which, as shown in FIG. 5, an organic solvent to be treated 20 is first passed through an H-type cation exchanger-packed column 1 which is packed with an H-type cation exchanger (H-type chelate exchanger (1a) or H-type strongly acidic cation exchanger (1b)), and then a treated liquid which has been treated through the H-type cation exchanger-packed column 1 is passed through a multiple bed-packed column 14 in which there are laminated and packed in order a "first repeating unit 13a composed of a layer 11a of the anion exchanger (2) as a prestage and a layer 12a of the H-type strongly acidic cation exchanger (3) as a poststage" and a "second repeating unit 13b composed of a layer 11b of the anion exchanger (2) as a prestage and a layer 12b of the H-type strongly acidic cation exchanger (3) as a poststage", to thereby obtain a purified organic solvent 23. In the form example shown in FIG. 5, the range indicated by Reference Sign 21 is the first treatment step, and the range indicated by Reference Sign 22 is the second treatment step. Here, in the form example shown in FIG. 5, there has been shown an example in which there is twice repeated the repeating unit composed of the layer of the anion exchanger (2) as a prestage and the layer of the H-type strongly acidic cation exchanger (3) as a poststage, but there may be three or more times repeated the repeating unit composed of the layer of the anion exchanger (2) as a prestage and the layer of the H-type strongly acidic cation exchanger (3) as a poststage.

A method for purifying an organic solvent according to a third embodiment of the present invention is a method for purifying an organic solvent comprising a treatment step (3) of bringing an organic solvent to be treated into contact with a mixed bed of an H-type chelate exchanger (1a), an anion exchanger (2) and an H-type strongly acidic cation exchanger (3).

The treatment step (3) involved in the method for purifying an organic solvent according to the third embodiment of the present invention is a step of bringing the organic solvent to be treated into contact with a mixed bed of the H-type chelate exchanger (1a), the anion exchanger (2) and the H-type strongly acidic cation exchanger (3).

The organic solvent to be treated, the H-type chelate exchanger (1a), the anion exchanger (2) and the H-type strongly acidic cation exchanger (3) involved in the method for purifying an organic solvent according to the third embodiment of the present invention are the same as the organic solvent to be treated, the H-type chelate exchanger (1a), the anion exchanger (2) and the H-type strongly acidic cation exchanger (3) involved in the method for purifying an organic solvent according to the first embodiment of the present invention.

The mixed bed of the H-type chelate exchanger (1a), the anion exchanger (2) and the H-type strongly acidic cation exchanger (3) involved in the method for purifying an organic solvent according to the third embodiment of the present invention is composed of a mixture of the H-type chelate exchanger (1a), the anion exchanger (2) and the H-type strongly acidic cation exchanger (3). Here, in the case where the H-type chelate exchanger (1a) is the H-type organic porous chelate exchanger, there is used the H-type organic porous chelate exchanger having a shape cut out into an optional size, for example, a cube of about 3 mm to about 10 mm in one side. In the case where the anion exchanger (2) is the organic porous anion exchanger, there is used the organic porous anion exchanger having a shape cut out into an optional size, for example, a cube of about 3 mm to about 10 mm in one side. Then, in the case where the H-type strongly acidic cation exchanger (3) is the organic porous strongly acidic cation exchanger, there is used the organic porous strongly acidic cation exchanger having a shape cut out into an optional size, for example, a cube of about 3 mm to about 10 mm in one side.

In the treatment step (3), by bringing the organic solvent to be treated into contact with the mixed bed of the H-type chelate exchanger (1a), the anion exchanger (2) and the H-type strongly acidic cation exchanger (3), the organic solvent to be treated is treated with the mixed bed of the H-type chelate exchanger (1a), the anion exchanger (2) and the H-type strongly acidic cation exchanger (3) to remove di- or higher-valent metals and monovalent metals in the organic solvent to be treated. Further in the treatment step (3), the anion exchanger (2) removes the mineral acid released from the H-type chelate exchanger (1a) to the organic solvent to be treated.

In the treatment step (3), the liquid passing velocity (SV) when the organic solvent to be treated is passed through the mixed bed of the H-type chelate exchanger (1a), the anion exchanger (2) and the H-type strongly acidic cation exchanger (3) is not especially limited, and is suitably selected, but is preferably 0.1 to 100 $h^{-1}$, especially preferably 2 to 30 $h^{-1}$ and further preferably 4 to 25 $h^{-1}$.

In the treatment step (3), the temperature when the organic solvent to be treated is passed through the mixed bed (3) of the H-type chelate exchanger (1a), the anion exchanger (2) and the H-type strongly acidic cation exchanger (3) is not especially limited, and is suitably selected, but is usually 0 to 50° C. Then, depending on the kind of the organic solvent to be treated, in the treatment step (3), the organic solvent to be treated may also be passed through the mixed bed of the H-type chelate exchanger (1a), the anion exchanger (2) and the H-type strongly acidic cation exchanger (3) at 0 to 80° C. In the case where in the treatment step (3), the organic solvent to be treated is passed through the mixed bed of the H-type chelate exchanger (1a), the anion exchanger (2) and the H-type strongly acidic cation exchanger (3) at 0 to 80° C., since the strongly basic anion exchanger (2a), when being used as the anion exchanger (2), is easily decomposed, the weakly basic anion exchanger (2b) is used as the anion exchanger (2).

Examples of the method for purifying an organic solvent according to the third embodiment of the present invention include, as shown in FIG. 6, a method in which an organic solvent to be treated 20 is passed through a mixed bed-packed column 24 which is packed with a mixture of the H-type chelate exchanger (1a), the anion exchanger (2) and the H-type strongly acidic cation exchanger (3) to thereby obtain a purified organic solvent 23. In the form example shown in FIG. 6, the range indicated by Reference Sign 25 is the treatment step (3).

In the method for purifying an organic solvent according to the first embodiment of the present invention or the method for purifying an organic solvent according to the third embodiment of the present invention, the proportion ((volume of the anion exchanger (2)/volume of the H-type chelate exchanger (1a))×100) of the volume of the anion exchanger (2) to the volume of the H-type chelate exchanger (1a) is preferably 0.1 to 99.0% by volume, more preferably 0.1 to 70.0% by volume and especially preferably 0.1 to 50.0% by volume.

In the method for purifying an organic solvent according to the first embodiment of the present invention or the method for purifying an organic solvent according to the third embodiment of the present invention, the proportion ((volume of the strongly acidic cation exchanger (3)/volume of the H-type chelate exchanger (1a))×100) of the volume of the strongly acidic cation exchanger (3) to the volume of the H-type chelate exchanger (1a) is preferably 0.1 to 99.0% by volume, more preferably 0.1 to 70.0% by volume and especially preferably 0.1 to 50.0% by volume.

With regard to the H-type cation exchanger (H-type chelate exchanger (1a), strongly acidic cation exchanger (1b)), the anion exchanger (2) and the H-type strongly acidic cation exchanger (3), a substrate to which ion-exchange groups are to be introduced may also be an organic porous material. The organic porous material involved in the present invention will be described hereinafter.

To the organic porous ion exchanger, an H-type chelate exchange group, a strongly acidic cation-exchange group or an anion-exchange group has been introduced. That is, an organic porous material having an H-type chelate exchange group introduced thereto is the H-type organic porous chelate exchanger (1a); an organic porous material having an H-type strongly acidic cation-exchange group introduced thereto is the H-type organic porous strongly acidic cation exchanger (1b) or (3); and an organic porous material having an anion-exchange group introduced thereto is the organic porous anion exchanger. Here, the functional groups introduced to the organic porous ion exchangers are the same as the functional groups introduced to the above-mentioned (H-type chelate exchanger (1a), strongly acidic cation exchanger (1b)), anion exchanger (2) or H-type strongly acidic cation exchanger (3).

Examples of the organic porous ion exchanger include an organic porous ion exchanger (hereinafter, described also as an organic porous ion exchanger according to the first embodiment) which is composed of continuous skeleton phases and continuous pore phases, has a thickness of the continuous skeleton of 1 to 100 μm and a mean diameter of the continuous pore of 1 to 1,000 μm, has a total pore volume of 0.5 to 50 mL/g, has ion-exchange groups (chelate exchange group, H-type strongly acidic cation-exchange group or anion-exchange group) introduced thereto, and has an ion-exchange capacity per weight in a dry state of 1 to 6 mg eq/g, wherein the ion-exchange groups are distributed uniformly in the organic porous ion exchanger.

The organic porous ion exchanger according to the first embodiment includes an organic porous ion exchanger which has a continuous pore structure in which bubble-like macropores overlap and the overlapping portions become apertures of 1 to 1,000 μm in mean diameter, has a total pore volume of 1 to 50 mL/g, has ion-exchange groups introduced thereto, and has an ion-exchange capacity per weight in a dry state of 1 to 6 mg eq/g, wherein the ion-exchange groups are distributed uniformly in the organic porous ion exchanger.

Then, the organic porous ion exchanger according to the first embodiment includes an organic porous ion exchanger which has a continuous macropore structure in which bubble-like macropores overlap and the overlapping portions become apertures of 30 to 300 μm in mean diameter, has a total pore volume of 0.5 to 10 mL/g, has cation-exchange groups or anion-exchange groups introduced thereto, and has an ion-exchange capacity per weight in a dry state of 1 to 6 mg eq/g, wherein the ion-exchange groups are distributed uniformly in the organic porous ion exchanger, and in a SEM image of a cut surface of the continuous macropore structure (dried one), the area of skeleton portions appearing on the cut surface is 25 to 50% in the image region.

Then, the organic porous ion exchanger according to the first embodiment includes an organic porous ion exchanger which is a co-continuous structure composed of: a three-dimensionally continuing skeleton of 1 to 60 μm in mean thickness composed of an aromatic vinyl polymer containing 0.1 to 5.0% by mol of a crosslinked structural unit in the whole structural unit having ion-exchange groups (chelate exchange groups, H-type strongly acidic cation-exchange groups or anion-exchange groups) introduced thereto; and three-dimensionally continuing pores of 10 to 200 μm in mean diameter among the skeleton, and which has a total pore volume of 0.5 to 10 mL/g, has cation-exchange groups introduced thereto, and has an ion-exchange capacity per weight in a dry state of 1 to 6 mg eq/g, wherein the ion-exchange groups are distributed uniformly in the organic porous ion exchanger.

The content of each metal in the purified organic solvents obtained by the method for purifying an organic solvent according to the first embodiment of the present invention, the method for purifying an organic solvent according to the second embodiment of the present invention and the method for purifying an organic solvent according to the third embodiment of the present invention is selected suitably according to the applications of the organic solvent after being purified, and is preferably 10 ppt by mass or lower for any each metal. That is, the content of each di- or higher-valent metal in the purified organic solvent obtained by the method for purifying an organic solvent according to the first embodiment of the present invention, the method for purifying an organic solvent according to the second embodiment of the present invention and the method for purifying an organic solvent according to the third embodiment of the present invention is selected suitably according to the applications of the organic solvent after being purified, and is preferably 10 ppt by mass or lower for each metal; and the content of each monovalent metal therein is selected suitably according to the applications of the organic solvent after being purified, and is preferably 10 ppt by mass or lower for any each metal. The applications of the purified organic solvent obtained by carrying out the method for purifying an organic solvent according to the first embodiment of the present invention, the method for purifying an organic solvent according to the second embodiment of the present invention and the method for purifying an organic solvent according to the third embodiment of the present invention include diluting solvents, dissolving solvents, washing solvents, drying solvents and the like in semiconductor production processes. Further, according to the method for purifying an organic solvent according to the first embodiment of the present invention, the method for purifying an organic solvent according to the second embodiment of the present invention and the method for purifying an organic solvent according to the third embodiment of the present invention, since purification in an impurity level of 1 ppt by mass or lower is made possible, the purified organic solvent obtained by carrying out the method for purifying an organic solvent according to the first embodiment of the present invention, the method for purifying an organic solvent according to the second embodiment of the present invention and the method for purifying an organic solvent according to the third embodiment of the present invention are suitably used as diluting solvents (blank solutions for calibration curves) for standard solutions to be used for preparation of calibration curves for trace metal analysis, sample diluting solvents, and washing solvents for implements and analyzers.

An apparatus for purifying an organic solvent according to the first embodiment of the present invention is an apparatus for purifying an organic solvent comprising a single bed of the H-type cation exchanger (1) through which an organic solvent to be treated is passed, and a mixed bed of the anion exchanger (2) and the H-type strongly acidic cation exchanger (3) through which a treated liquid from the single bed of the H-type cation exchanger (1) is passed.

The flow of the apparatus for purifying an organic solvent according to the first embodiment of the present invention includes a form example shown in FIG. 1.

An apparatus for purifying an organic solvent according to the second embodiment of the present invention is an apparatus for purifying an organic solvent comprising a single bed of the H-type cation exchanger (1) through which an organic solvent to be treated is passed, a single bed of the anion exchanger (2) through which a treated liquid from the single bed of the H-type cation exchanger (1) is passed, and a single bed of the H-type strongly acidic cation exchanger (3) through which a treated liquid from the single bed of the anion exchanger (2) is passed.

The flow of the apparatus for purifying an organic solvent according to the second embodiment of the present invention includes a form example shown in FIG. 2.

An apparatus for purifying an organic solvent according to the third embodiment of the present invention is an apparatus for purifying an organic solvent comprising a single bed of the H-type cation exchanger (1) through which an organic solvent to be treated is passed, and a multiple bed, composed of a layer of the anion exchanger (2) as a prestage and a layer of the H-type strongly acidic cation exchanger (3) as a poststage through which a treated liquid from the single bed of the H-type cation exchanger (1) is passed.

The flow of the apparatus for purifying an organic solvent according to the third embodiment of the present invention includes a form example shown in FIG. 3.

The apparatuses for purifying an organic solvent according to the first to third embodiments of the present invention include apparatuses for purifying an organic solvent in which the H-type cation exchanger (1) is the H-type chelate exchanger. Further the apparatuses for purifying an organic solvent according to the first to third embodiments of the present invention include apparatuses for purifying an organic solvent in which the H-type cation exchanger (1) is the H-type strongly acidic cation exchanger.

An apparatus for purifying an organic solvent according to a fourth embodiment of the present invention is an apparatus for purifying an organic solvent comprising a mixed bed of an H-type chelate exchanger, an anion exchanger (2) and an H-type strongly acidic cation exchanger (3) through which an organic solvent to be treated is passed.

The flow of the apparatus for purifying an organic solvent according to the fourth embodiment of the present invention includes a form example shown in FIG. 6.

The apparatus for purifying an organic solvent according to the fourth embodiment of the present invention includes an apparatus for purifying an organic solvent in which the H-type cation exchanger (1) is the H-type chelate exchanger.

The H-type cation exchanger (1), the anion exchanger (2) and the H-type strongly acidic cation exchanger (3) involved in the apparatuses for purifying an organic solvent according to the first to fourth embodiments of the present invention are the same as the H-type cation exchanger (1), the anion exchanger (2) and the H-type strongly acidic cation exchanger (3) involved in the methods for purifying an organic solvent according to the first to third embodiments of the present invention.

In the apparatuses for purifying an organic solvent according to the first to fourth embodiments of the present invention, in the case where the H-type cation exchanger (1) is the H-type chelate exchanger, the proportion ((volume of the anion exchanger (2)/volume of the H-type chelate exchanger (1a))×100) of the volume of the anion exchanger (2) to the volume of the H-type chelate exchanger (1a) is preferably 0.1 to 99.0% by volume, more preferably 0.1 to 70.0% by volume and especially preferably 0.1 to 50.0% by volume.

In the apparatuses for purifying an organic solvent according to the first to fourth embodiments of the present invention, in the case where the H-type cation exchanger (1) is the H-type chelate exchanger, the proportion ((volume of the strongly acidic cation exchanger (3)/volume of the H-type chelate exchanger (1a))×100) of the volume of the strongly acidic cation exchanger (3) to the volume of the H-type chelate exchanger (1a) is preferably 0.1 to 99.0% by volume, more preferably 0.1 to 70.0% by volume and especially preferably 0.1 to 50.0% by volume.

Hitherto, embodiments of the present invention have been described, but the present invention is not any more limited thereto, and various changes, additions and the like may be made without departing the spirit of the invention. For example, although in FIG. 1 to FIG. 5, the first treatment step and the second treatment step are carried out by using linked two or more packed columns, the first treatment step and the second treatment step may be carried out by using one packed column in which there is formed a multiple bed in which a bed to carry out the first treatment step is packed as a prestage and a bed to carry out the second treatment step is packed as a poststage. There is a form example thereof composed of a multiple bed in which a bed of the H-type chelate exchanger (1a) is packed in a prestage of one column and a mixed bed of the anion exchanger (2) and the H-type strongly acidic cation exchanger (3) is packed in a poststage thereof. In this case, the first treatment step is carried out by the bed of the H-type chelate exchanger (1a) as a prestage and the second treatment step is carried out by the mixed bed of the anion exchanger (2) and the H-type strongly acidic cation exchanger (3) as a poststage.

EXAMPLES

Hereinafter, the present invention will be described in detail by way of Examples, but the present invention is not any more limited to the following Examples.

Reference Example 1

An H-type chelate exchange resin (DS-21) (50 mL) was packed in a column of 16 mm in inner diameter and 300 mm in height. Then, an isopropyl alcohol (IPA) having a water content of 20 ppm by mass or lower was passed from an upper part of the column toward a lower part thereof; and the liquid passing was continued until the water content at an outlet decreased to 30 ppm by mass to replace the water content in the resin by IPA.

Then, an IPA simulation liquid 1 was passed to the column at SV of 5 $h^{-1}$ and when 20 BV (volume 20 times the resin volume) was passed, a treated liquid was sampled.

Then, for the obtained treated liquid, the metal contents were measured by Agilent 8900 ICP-QQQ (manufactured by Agilent Technologies, Inc.). The results are shown in Table 2. Then, the water contents of the IPA simulation liquid and the treated liquid were measured and were confirmed to be 30 ppm by mass or lower for either.

Then, similarly, an IPA simulation liquid 2 was passed. The results are shown in Table 2.

The H-type chelate exchange resin: an H-type aminophosphoric acid-type chelate resin (Orlite DS-21 (cation-exchange capacity: 1.8 eq/L-Resin, harmonic mean diameter: 500 μm), manufactured by Organo Corp.)

<The IPA Simulation Liquids>

A standard solution for ICP-AES/ICP-MS, an organometal standard solution: Conostan with a paraffin oil base (manufactured by Conostan Co.) was added to an IPA XE (manufactured by Tokuyama Corp.) to thereby prepare the IPA simulation liquid 1 of 1,000 ppt by mass. Then, similarly, the IPA simulation liquid 2 of 100 ppt by mass was prepared. Each metal content in the IPA simulation liquids is shown in Table 1.

TABLE 1

<Each metal content in the IPA simulation liquids>

| | Metal content (ppt by mass) | |
|---|---|---|
| | the IPA simulation liquid 1 | the IPA simulation liquid 2 |
| Na | 1067 | 128 |
| K | 1046 | — |
| Cr | 1056 | 110 |
| Fe | 999 | 119 |

<Measurement of Water Content>

The water content was measured by using an Aquacounter AQ-2200 (manufactured by Hiranuma Sangyo Corp.).

TABLE 2

<Removal performance of the chelate exchange resin>

| | Content (ppt by mass) the IPA simulation liquid 1 |
|---|---|
| Na | <5 |
| K | 13 |
| Cr | 36 |
| Fe | 33 |

Example 1

50 mL of a mixture of the H-type chelate exchange resin (DS-21), an OH-type strongly basic anion-exchange resin (DS-2) and an H-type strongly acidic cation-exchange resin (DS-1) in a proportion of 3:1:1 was packed in a column of 16 mm in inner diameter and 300 mm in height (H-type C/OH-type A/H-type K mixed bed 1).

Then, the IPA simulation liquid 2 was passed at SV of 5 $h^{-1}$ through the H-type C/OH-type A/H-type K mixed bed 1, and when 20 BV (volume 20 times the resin volume) was passed, a treated liquid was sampled.

Then, the metal contents of the obtained treated liquid were measured. The results are shown in Table 3.

The OH-type strongly basic anion-exchange resin (DS-2): manufactured by Organo Corp. (anion-exchange capacity: 1.0 eq/L-Resin)

The H-type strongly acidic cation-exchange resin (DS-1): manufactured by Organo Corp. (cation-exchange capacity: 2.0 eq/L-Resin)

Example 2

30 mL of the H-type chelate exchange resin (DS-21) was packed in a column of 16 mm in inner diameter and 300 mm in height (H-type C single bed 1). Further, the OH-type strongly basic anion-exchange resin (DS-2) was packed as a prestage in a column of 16 mm in inner diameter and 300 mm in height and the H-type strongly acidic cation-exchange resin (DS-1) was packed as a poststage in the column in a stage layer thickness ratio of 1:1 in a total volume of the both of 20 mL (OH-type A/H-type K multiple bed 1). Then, the H-type C single bed as the prestage and the OH-type A/H-type K multiple bed 1 as the poststage were linked.

Then, the IPA simulation liquid 2 was passed at SV of 5 $h^{-1}$ through the H-type C single bed 1 as the prestage and the OH-type A/H-type K multiple bed 1 as the poststage, and when 20 BV (volume 20 times the resin volume) was passed, a treated liquid was sampled.

Then, the metal contents of the obtained treated liquid were measured. The results are shown in Table 3.

Comparative Example 1

50 mL of the H-type strongly acidic cation-exchange resin (DS-1) was packed in a column of 16 mm in inner diameter and 300 mm in height (H-type K single bed 1).

Then, the IPA simulation liquid 1 was passed at SV of 5 $h^{-1}$ through the H-type K single bed 1, and when 20 BV (volume 20 times the resin volume) was passed, a treated liquid was sampled.

Then, the metal contents of the obtained treated liquid were measured. The results are shown in Table 3.

Comparative Example 2

50 mL of a mixture of the OH-type strongly basic anion-exchange resin (DS-2) and the H-type strongly acidic cation-exchange resin (DS-1) in a volume proportion of 1:1 was packed in a column of 16 mm in inner diameter and 300 mm in height (OH-type A/H-type K mixed bed 1).

Then, the IPA simulation liquid 1 was passed at SV of 5 $h^{-1}$ through the OH-type A/H-type K mixed bed 1, and when 20 BV (volume 20 times the resin volume) was passed, a treated liquid was sampled.

Then, the metal contents of the obtained treated liquid were measured. The results are shown in Table 3.

Comparative Example 3

30 mL of the H-type chelate exchange resin (DS-21) was packed in a column of 16 mm in inner diameter and 300 mm in height (H-type C single bed 1). Further, 20 mL of the OH-type strongly basic anion-exchange resin (DS-2) was packed in a column of 16 mm in inner diameter and 300 mm in height (OH-type A single bed 1). Then, the H-type C single bed 1 as a prestage and the OH-type A single bed 1 as a poststage were linked.

Then, the IPA simulation liquid 2 was passed at SV of 5 $h^{-1}$ through the H-type C single bed 1 as a prestage and the OH-type A single bed 1 as a poststage, and when 20 BV (volume 20 times the resin volume) was passed, a treated liquid was sampled.

Then, the metal contents of the obtained treated liquid were measured. The results are shown in Table 3.

Comparative Example 4

50 mL of the OH-type strongly basic anion-exchange resin (DS-2) was packed in a column of 16 mm in inner diameter and 300 mm in height (OH-type A single bed 1).

Then, the IPA simulation liquid 1 was passed at SV of 5 $h^{-1}$ through the OH-type A single bed 1, and when 20 BV (volume 20 times the resin volume) was passed, a treated liquid was sampled.

Then, the metal contents of the obtained treated liquid were measured. The results are shown in Table 3.

TABLE 3

| | Metal content (ppt by mass) | | | | | |
|---|---|---|---|---|---|---|
| | Example 1 | Example 2 | Comparative Example 1 | Comparative Example 2 | Comparative Example 3 | Comparative Example 4 |
| IPA simulation liquid No. | 2 | 2 | 1 | 1 | 2 | 1 |
| Na | <5 | <5 | <5 | 100 | 22 | 911 |
| Cr | <5 | <5 | 89 | 131 | <5 | 43 |
| Fe | <5 | <5 | 54 | 116 | <5 | 223 |

Examples 3 to 6

Operations were carried out as in Example 1, except for carrying out the liquid passing at SV indicated in Table 4 instead of carrying out the liquid passing at SV of 5 h$^{-1}$. The results are shown in Table 4.

TABLE 4

| | Metal content (ppt by mass) | | | |
|---|---|---|---|---|
| | Example 3 | Example 4 | Example 5 | Example 6 |
| SV (h$^{-1}$) | 10 | 20 | 30 | 40 |
| Na | <5 | <5 | <5 | <5 |
| K | <5 | <5 | <5 | <5 |
| Cr | <5 | <5 | 11 | 42 |
| Fe | <5 | <5 | 13 | 46 |

Comparative Example 5

36 mL of the H-type strongly acidic cation-exchange resin (DS-1) was packed in a column of 16 mm in inner diameter and 300 mm in height (H-type K single bed 1). Then, an IPA simulation liquid 3 (indicated in Table 5) was passed at SV of 5 h$^{-1}$, and when 20 BV (volume 20 times the resin volume) was passed, a treated liquid was sampled.

Then, the metal contents of the obtained treated liquid were measured. The results are shown in Table 6.

Example 7

18 mL of an H-type strongly acidic cation-exchange resin (DS-1) was packed as a prestage in a column of 16 mm in inner diameter and 300 mm in height, and 18 mL of a mixed bed of 9 mL of the H-type strongly acidic cation-exchange resin (DS-1) and 9 mL of an OH-type strongly basic anion-exchange resin (DS-2) was packed as a poststage in the column, in a stage layer thickness ratio of 1:1 in a total volume of 36 mL (H-type K/H-type, OH-type mixed bed 1).

Then, an IPA simulation liquid 4 (indicated in Table 5) was passed through the H-type K/H-type, OH-type mixed bed 1 at SV of 5 h$^{-1}$, and when 20 BV (volume 20 times the resin volume) was passed, a treated liquid was sampled.

Then, the metal contents of the obtained treated liquid were measured. The results are shown in Table 6.

The H-type strongly acidic cation-exchange resin (DS-1): manufactured by Organo Corp. (cation-exchange capacity: ≥2.1 eq/L-Resin)

The OH-type strongly basic anion-exchange resin (DS-2): manufactured by Organo Corp. (anion-exchange capacity: ≥1.0 eq/L-Resin)

TABLE 5

<Each metal content in the IPA simulation liquids>

| | Example 7 Metal content in the IPA simulation liquid 3 (ppt by mass) | Comparative Example 5 Metal content in the IPA simulation liquid 4 (ppt by mass) |
|---|---|---|
| Al | 113 | 102 |
| As | 102 | 91 |
| Y | 81 | 98 |
| Zr | 78 | 97 |
| Ru | 98 | 88 |
| Rh | 101 | 90 |
| Pd | 100 | 95 |
| Sb | 103 | 97 |
| Ba | 87 | 90 |
| La | 118 | 210 |
| Ce | 113 | 184 |
| Pr | 109 | 160 |
| Nd | 106 | 134 |
| Sm | 102 | 77 |
| Eu | 90 | 77 |
| Gd | 99 | 129 |
| Tb | 90 | 89 |
| Dy | 89 | 88 |
| Ho | 89 | 89 |
| Er | 86 | 93 |
| Tm | 87 | 90 |
| Yb | 85 | 92 |
| Lu | 87 | 87 |
| Hf | 83 | 89 |
| Ta | 95 | 86 |
| W | 120 | 101 |
| Re | 104 | 94 |
| Ir | 94 | 88 |
| Pt | 83 | 79 |
| Hg | 127 | 138 |
| Th | 200 | 331 |

| | Example 7 Metal content in the treated liquid (ppt by mass) | Comparative Example 5 Metal content in the treated liquid (ppt by mass) |
|---|---|---|
| SV (h$^{-1}$) | 5 | 5 |
| Al | <10 | 13 |
| As | <10 | 84 |
| Y | <10 | 55 |
| Zr | <10 | 49 |
| Ru | <10 | 73 |
| Rh | <10 | 86 |
| Pd | <10 | 54 |
| Sb | <10 | 69 |
| Ba | <10 | 26 |
| La | <10 | 95 |
| Ce | <10 | 79 |
| Pr | <10 | 67 |
| Nd | <10 | 44 |
| Sm | <10 | 22 |

-continued

| | Example 7 Metal content in the treated liquid (ppt by mass) | Comparative Example 5 Metal content in the treated liquid (ppt by mass) |
|---|---|---|
| Eu | <10 | 18 |
| Gd | <10 | 48 |
| Tb | <10 | 28 |
| Dy | <10 | 27 |
| Ho | <10 | 27 |
| Er | <10 | 29 |
| Tm | <10 | 31 |
| Yb | <10 | 32 |
| Lu | <10 | 31 |
| Hf | <10 | 37 |
| Ta | <10 | 15 |
| W | <10 | 31 |
| Re | <10 | 77 |
| Ir | <10 | 68 |
| Pt | <10 | 51 |
| Hg | <10 | 50 |
| Th | <10 | 198 |

REFERENCE SIGNS LIST

1 H-TYPE CATION EXCHANGER-PACKED COLUMN
2, 24 MIXED BED-PACKED COLUMN
3, 8a, 8b ANION EXCHANGER-PACKED COLUMN
4, 9a, 9b STRONGLY ACIDIC CATION EXCHANGER-PACKED COLUMN
5, 11a, 11b LAYER OF ANION EXCHANGER
6, 12a, 12b LAYER OF H-TYPE STRONGLY ACIDIC CATION EXCHANGER
7, 14 MULTIPLE BED-PACKED COLUMN
10a, 10b, 13a, 13b REPEATING UNIT
20 ORGANIC SOLVENT TO BE TREATED
21 FIRST TREATMENT STEP
22 SECOND TREATMENT STEP
23 TREATED LIQUID
25 TREATMENT STEP (3)

The invention claimed is:

1. A method for purifying an organic solvent, the organic solvent being an organic solvent used in semiconductor production processes or for trace metal analysis, comprising:
 a first treatment of bringing the organic solvent into contact with an H-type cation exchanger to form a treated liquid; and
 a second treatment of bringing the treated liquid from the first treatment into contact with an anion exchanger and an H-type strongly acidic cation exchanger,
 wherein the H-type cation exchanger is an H-type chelate exchanger.

2. The method for purifying the organic solvent according to claim 1, wherein the second treatment is carried out by passing the treated liquid from the first treatment through a mixed bed of the anion exchanger and the H-type strongly acidic cation exchanger.

3. The method for purifying the organic solvent according to claim 1, wherein the second treatment is carried out by first bringing the treated liquid from the first treatment into contact with the anion exchanger, and then bringing the treated liquid into contact with the H-type strongly acidic cation exchanger.

4. The method for purifying the organic solvent according to claim 1, wherein a functional group of the H-type chelate exchanger is an iminodiacetic acid group, an aminomethylphosphoric acid group or an iminopropionic acid group.

5. The method for purifying the organic solvent according to claim 1, wherein a proportion of a volume of the anion exchanger to a volume of the H-type chelate exchanger is 0.1 to 99.0% by volume.

6. The method for purifying the organic solvent according to claim 1, wherein a proportion of a volume of the cation exchanger to a volume of the H-type chelate exchanger is 0.1 to 99.0% by volume.

7. The method for purifying the organic solvent according to claim 1, wherein the organic solvent is a polar organic solvent.

8. A method for purifying an organic solvent, the organic solvent being an organic solvent used in semiconductor production processes or for trace metal analysis, comprising:
 a first treatment step of bringing the organic solvent into contact with an H-type cation exchanger to form a treated liquid; and
 a second treatment step of bringing the treated liquid from the first treatment step into contact with an anion exchanger and an H-type strongly acidic cation exchanger,
 wherein the H-type cation exchanger is an H-type strongly acidic cation exchanger.

9. The method for purifying an organic solvent according to claim 8, wherein the second treatment step is carried out by passing the treated liquid from the first treatment step through a mixed bed of the anion exchanger and the H-type strongly acidic cation exchanger.

10. The method for purifying an organic solvent according to claim 8, wherein the second treatment step is carried out by first bringing the treated liquid from the first treatment step into contact with the anion exchanger, and then bringing the treated liquid into contact with the H-type strongly acidic cation exchanger.

11. The method for purifying an organic solvent according to claim 8, wherein the organic solvent is a polar organic solvent.

* * * * *